(12) United States Patent
Conway et al.

(10) Patent No.: US 6,304,629 B1
(45) Date of Patent: *Oct. 16, 2001

(54) COMPACT SCANNER APPARATUS AND METHOD

(76) Inventors: Granville Todd Conway, Village Rd. Green Village, Harding Township, NJ (US) 07935; Michael Patrick Maes, 24 Belle Vista Ave., Saddlebrook, NJ (US) 07663; Bradley Livingston Conway, 19 Peachcroft Rd., Morristown, NJ (US) 07960

( * ) Notice: Subject to any disclaimer, the term of this patent is extended or adjusted under 35 U.S.C. 154(b) by 0 days.

This patent is subject to a terminal disclaimer.

(21) Appl. No.: 09/516,468

(22) Filed: Mar. 1, 2000

Related U.S. Application Data

(60) Continuation-in-part of application No. 09/164,986, filed on Sep. 23, 1998, now Pat. No. 6,058,159, which is a division of application No. 08/584,469, filed on Jan. 11, 1996, now abandoned.

(51) Int. Cl.[7] .................................................. G21F 5/01
(52) U.S. Cl. .................. 378/68; 198/502.1; 198/950; 250/359.1; 250/453.11; 250/491.1; 378/57
(58) Field of Search .......................... 198/502.1, 502.2, 198/840, 841, 950, 358.1, 359.1, 453.11, 491.1, 506.1; 250/519.1, 57, 68, 98.2, 98.6; 378/208

(56) References Cited

U.S. PATENT DOCUMENTS

| Re. 36,943 | * | 7/2000 | Atwell et al. ...................... 250/358.1 |
| 6,088,423 | * | 7/2000 | Krug et al. .............................. 378/57 |
| 6,205,195 | * | 3/2001 | Lanza .................................... 376/157 |
| 6,218,943 | * | 4/2001 | Ellenbogen ........................ 340/572.4 |

* cited by examiner

Primary Examiner—Christopher P. Ellis
Assistant Examiner—Joe Dillon, Jr.

(57) ABSTRACT

A scanner comprises a conveyor device, a tunnel housing, a bed assembly housing, an isolating device, and one or two analysis devices. The tunnel housing, together with a top portion of the bed assembly housing, forms a substantially enclosed area for analyzing objects, and the bed assembly housing includes most of the components of the conveyor device. A frameless and coverless tunnel construction method clamps the frameless tunnel around the bed assembly housing, and uses a leaded curtain bracket and slot to increase the enclosed area within the tunnel housing for a given scanner width and height. For a coverless construction, the outside of the tunnel is finished cosmetically and any lead shielding is attached to the inside of the tunnel, instead of the outside. The conveyor device comprises a conveyor belt, rollers and a conveyor tracking device having first and second channels formed in first and second rails. The conveyor belt traverses a forward path and a return path in which the first and second rails are preferably provided. The isolating device comprises a first and a second curtain, which extend outward from first and second brackets. The first bracket and curtain are located at an entrance opening to the tunnel housing, and the second bracket and curtain are located at an exit opening of the tunnel housing. The brackets are adapted for insertion into a slot located in a portion of the housing. The isolating device temporarily seals off the substantially enclosed area formed by the tunnel housing and a top portion of the bed assembly housing. The scanning apparatus is light weight, compact, simpler and less expensive to construct and highly reliable in operation.

8 Claims, 11 Drawing Sheets

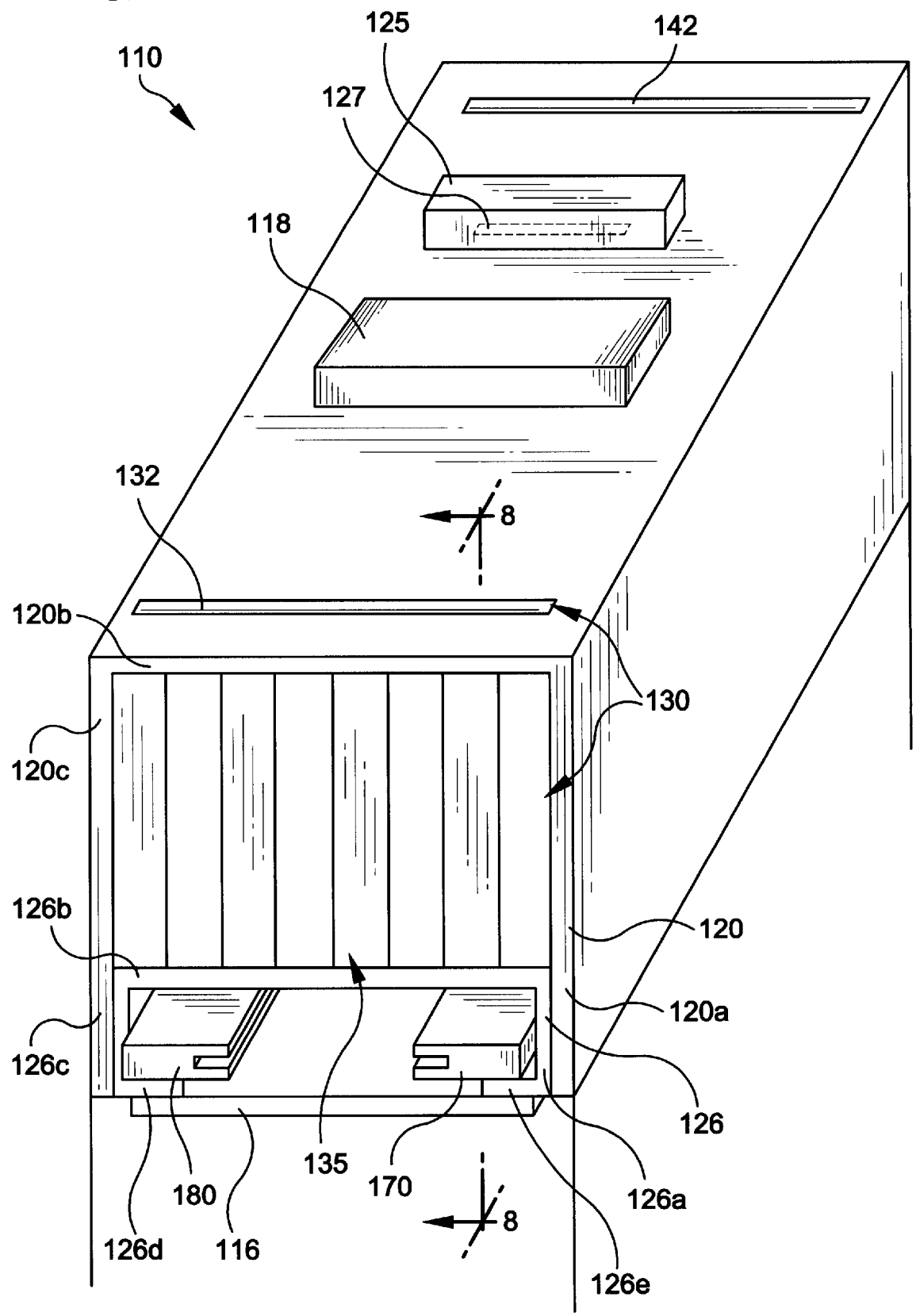

COMPACT SCANNER APPARATUS AND METHOD

CROSS REFERENCE TO RELATED APPLICATIONS

This application is a continuation-in-part of U.S. patent application Ser. No. 09/164,986 filed Sep. 23, 1998 issuing as U.S. Pat. No. 6,058.159 which is a divisional of U.S. patent application Ser. No. 08/584,469 which was filed on Jan. 11, 1996 now abandoned.

BACKGROUND OF THE INVENTION

1. Field of the Invention

This present invention relates to the field of relatively compact scanner apparatus and methods and more particularly to apparatus and methods for scanning objects which are transported by a conveyor belt through a temporarily sealed tunnel, such as in contraband detection systems.

2. Description of the Prior Art

Scanners, particularly "compact" scanners, are used for detecting contraband at schools, correctional mail screening, courthouse security, airport hand parcels, and industrial processing applications. These scanners employ tunnel housing, usually leaded and wired in part on the outside, an isolating device, a conveyor device, a bed assembly housing in which the conveyor device is substantially located, and framing and thinner painted covers to hide the unsightly framing and the lead. The tunnel housing typically has a top portion, and side portions which together with a top portion from the bed assembly housing, form a substantially enclosed area. The tunnel housing is also provided with entrance and exit openings to the substantially enclosed area.

The isolating device substantially covers the entrance and exit openings and is typically in the form of two separate lead curtains. One lead preferably fabric curtain is bolted to flat framing at the entrance opening, and the other lead preferably fabric curtain is bolted to flat framing located at the exit opening. Isolating devices permit the passage of conveyed objects into the substantially enclosed area formed by the tunnel housing and the top portion of the bed assembly housing, which is typically x-ray scatter lead shielded on the outside and may also substantially exclude light, noise, heat, cold, moisture, dryness, electrostatic or electromagnetic fields, dust gasses or chemical vapors while the conveyed objects are being analyzed.

Scanners analyze objects which are brought into the enclosed area formed by the tunnel housing and the top portion of the bed assembly housing by the conveyor device. The conveyor devices are typically comprised of relatively short lengthened conveyor belts. Short lengthened conveyor belts, particularly those with a relatively low length to width ratio, such as of less than twelve to one, 12 to 1, often mistrack causing damage to the conveyor belts, objects being scanned, and other parts of the system. Currently, expensive and elaborate tracking mechanisms such as precise construction of components, toothed or perforated belting to mesh with drive gears or belt grooves raised, profile rails, servo-drive tracking adjustment mechanisms, and reliance on a human attendant are used for tracking conveyor belts.

The framing provided to structurally connect the tunnel housing, the bed assembly housing, the conveyor device and the isolating device is often elaborate, wasteful, and space consuming, and requires a plurality of cover panels to hide the framing, the lead, the detector assembly and wiring. Scanners are needed which are more compact in overall width and length without sacrificing the width of the enclosed area inside the tunnel housing, and which are simpler and less costly to manufacture.

SUMMARY OF THE INVENTION

A compact and reliable scanning apparatus and method is provided. The scanner in one embodiment comprises a conveyor device, a tunnel housing, a bed assembly housing, an isolating device, and one or more analysis devices. The tunnel housing is comprised of top and side portions which together with a top portion from the bed assembly housing form a substantially enclosed area for analyzing objects. The bed assembly housing encloses most of the components of the conveyor device.

The conveyor device is typically comprised of a conveyor belt, rollers and a conveyor tracking device. The conveyor tracking device is preferably comprised of first and second channels formed in first and second rails, as taught in U.S. patent application Ser. No. 08/584,469, the disclosure of which is specifically incorporated herein by reference thereto. The conveyor belt, preferably includes a first edge and a second edge, and an inner surface and an outer surface. The first and second edges of the conveyor belt typically pass through the first and second channels formed in the first and second rails, respectively. The first and second rails inhibit the conveyor belt from misaligning. The conveyor belt preferably traverses a forward path and a return path and the first and second rails are preferably provided in the return path. The first and second rails are preferably opposite one another.

The isolating device is preferably comprised of separate first and second curtains which extend outward from separate first and second brackets, respectively. The first and second brackets and curtains are preferably adaptable for insertion into first and second slots, respectively, located in the top portion of the tunnel housing, near the entrance and exit openings, respectively. The slots can also be called slits. The brackets, the curtains, and the slots of the housing, are typically adaptable so that the curtains can be inserted into and through the appropriate slot but the brackets cannot be inserted through the appropriate slot. After the brackets and curtains have been inserted into their respective slot each curtain should entirely the cover either the exit or the entrance opening. The isolating device preferably temporarily seals off the substantially enclosed area bounded by the tunnel housing and the top portion of the bed assembly housing so that no X-rays will leak out.

In the preferred embodiment of the present invention the tunnel housing, the bed assembly housing, the conveyor device, the one or more analysis devices, and the isolating device are constructed in a manner which provides a largely frameless scanner apparatus. The bed assembly housing preferably comprises a top portion which is used as with the inverted U-shaped sheet metal housing to form a substantially enclosed area. The bed assembly housing further preferably comprises first and second side portions which are preferably fixed to the first and second side portions of the housing providing structural support and reducing the need for framing. One of the analysis devices may be comprised of detector housing metal members which are attached to the inside side and top of the frameless housing. In this way the long slits on two sides, which weaken the inverted U, are eliminated from conventional housing constructions. The slits appear instead in the thinner, substantially metal, detector housing members which form a side and the top of the tunnel. The analysis devices may be various types including X-ray or electromagnetic generators and detectors or vapour detectors.

The efficient construction of the conveyor device, the isolating device, the tunnel housing, the bed assembly housing, and the one or more analysis devices of the scanner maximizes the cross sectional area, and the width and height for the enclosed area formed by tunnel housing and the top portion of the bed assembly housing of the scanner for a given overall cross sectional width and height. In addition, the construction significantly simplifies and reduces the number of metal parts needed to frame, cover the framing, or otherwise make up the scanning device, decreasing its construction and operating costs.

BRIEF DESCRIPTION OF THE DRAWINGS

FIG. 11 is a perspective view of another embodiment of the scanner apparatus and method of the present invention, for convenience shown without rollers or its conveyer bed.

DETAILED DESCRIPTION OF INVENTION

Prior Art

Figure 1:
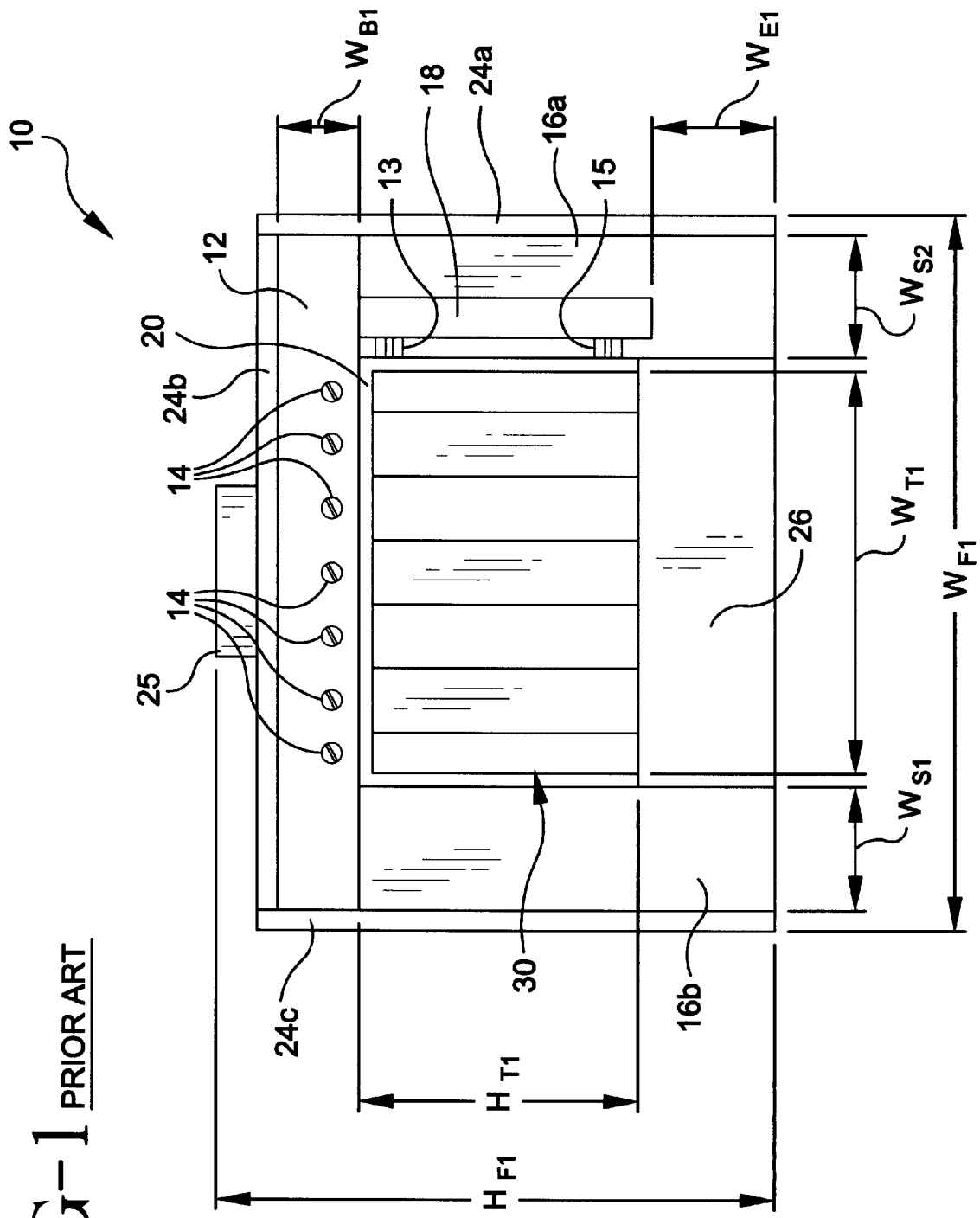
FIG. 1 is a frontal view of a prior art framed tunnel and under carriage.

A frontal view of a scanner 10 known in the prior art is shown in FIG. 1. The scanner 10 includes top framing 12, bolts 14, side framing 16a and 16b, detector tray assembly 18, tunnel housing 20, bed assembly housing 26, cosmetic panels 24a, 24b, and 24c, detector/generator 25 and isolating device portion 30.

The prior art scanner 10 has an overall height $H_{T1}$, and an overall width of $W_{F1}$. The area enclosed by the tunnel housing 20 and a top of the bed assembly housing 26 and covered by the isolating device portion 30 has a height of $H_{T1}$, and a width of $W_{F1}$. The tunnel housing 20 is usually leadlined on the outside. The side framing 16a and 16b ties or connects together the tunnel housing 20 and the bed assembly housing 26. The bed assembly housing 26 includes the motor, rollers, and the conveyor belt, for carrying items to be scanned, all of which are not shown. The scanner 10 of the prior art typically does not include a tracking mechanism to prevent the conveyor belt from misaligning. The top framing 12 ties the side framing 16a and 16b together and holds a heavy X-ray curtain bar, not shown, by use of bolts 14.

In order to allow the scanner 10 to be compact enough to fit through doors so that it can be transported and to consume less hallspace which can be scarce or expensive, there are limitations on the overall height $H_{T1}$, and the overall width $W_{F1}$ of the scanner 10. However, the top framing 12 also has to have a sufficient width $W_{F1}$ to allow mounting of the isolating device portion 30 and to provide structural support for the scanner 10. Similarly, side framing 16a and 16b have to have sufficient thickness to provide structural support for the scanner 10.

The frontal view of the scanner 10 in FIG. 1 shows only entrance framing into the enclosed area or tunnel bounded by tunnel housing 20 and the top of the bed assembly housing. However, the exit framing would be similar. Lengthwise framing would also be used (not shown) to connect the side framing 16a and 16b at the entrance with its counterpart side framing at the exit of the tunnel housing 20.

The tunnel housing 20 and framing typically supports at least the weight of leaded shielding and either an x-ray generator tubehead or a leaded steel detector tray (not shown). A detector/generator 25 is shown in FIG. 1. Conventional detectors of this type do not just utilize diagonally upshooting generators, but can utilize down shooting and side shooting generators, resulting only in a change of detector subassembly and slit/collimator locations. These alternate generator/detector configurations are not shown. The heavy framing supports the tunnel housing 20 and outside lead and spaces out and supports cosmetic panels 24a and 24c and top panel 24b, which often extend down well below the bed assembly 26 to casters, not shown. The prior art of baggage scanners are constructed in this heavily framed method which usually extends to casters or the ground, except for some smaller models, where the framing is sometimes separated below the bed assembly housing 26 to allow placement a table or a framed cart. In order to roll baggage scanners through narrow doorways, or to station them in narrow hallways, the available square tunnel space inside the area bounded by the tunnel housing 20 and the top of the bed assembly housing 26 left after designing in heavy framing becomes too light for many screened items, necessitating a still larger machine, or a slow and invasive individual visual parcel inspection by hand. Moreover, the framing which is typically welded and the cosmetic panels add complexity, cost and additional parts and labor.

The detector tray assemblies 18 are not used as a structural support or member for the tunnel housing 20 but rather is hung on the tunnel housing 20 such as by connectors 13 and 15.

DESCRIPTION OF THE PREFERRED EMBODIMENTS

Figure 2:
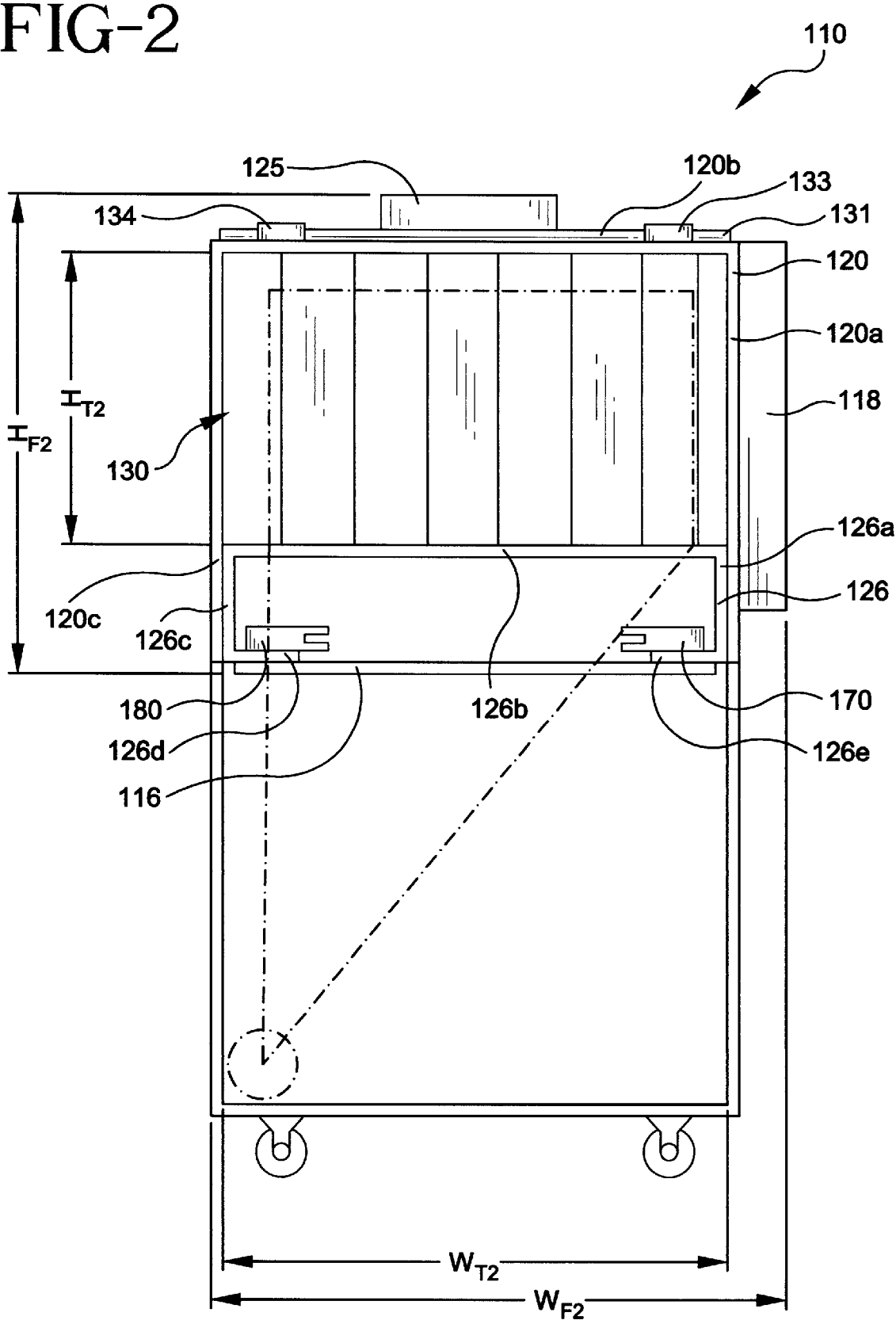
FIG. 2 is a frontal view of a scanner having a frameless housing, the scanner being shown without its rollers or a conveyor belt.

Referring to FIG. 2 of the drawings, the inverted U-shaped frameless sheet metal forming housing 110 is preferably as thick or thicker than conventionally used in framed scanner devices. It is clamped directly to the bed assembly housing and provides sufficient strength without framing members. The long x-ray slit which tends to weaken one side and/or the top of conventional scanner assemblies preferably appears, instead, within the side or side and top detector assemblies of the present scanner apparatus. These assemblies are preferably mounted on the inside of the inverted U housing. They can be constructed from thinner steel and form preferably one side and the top of the tunnel.

Figure 3:
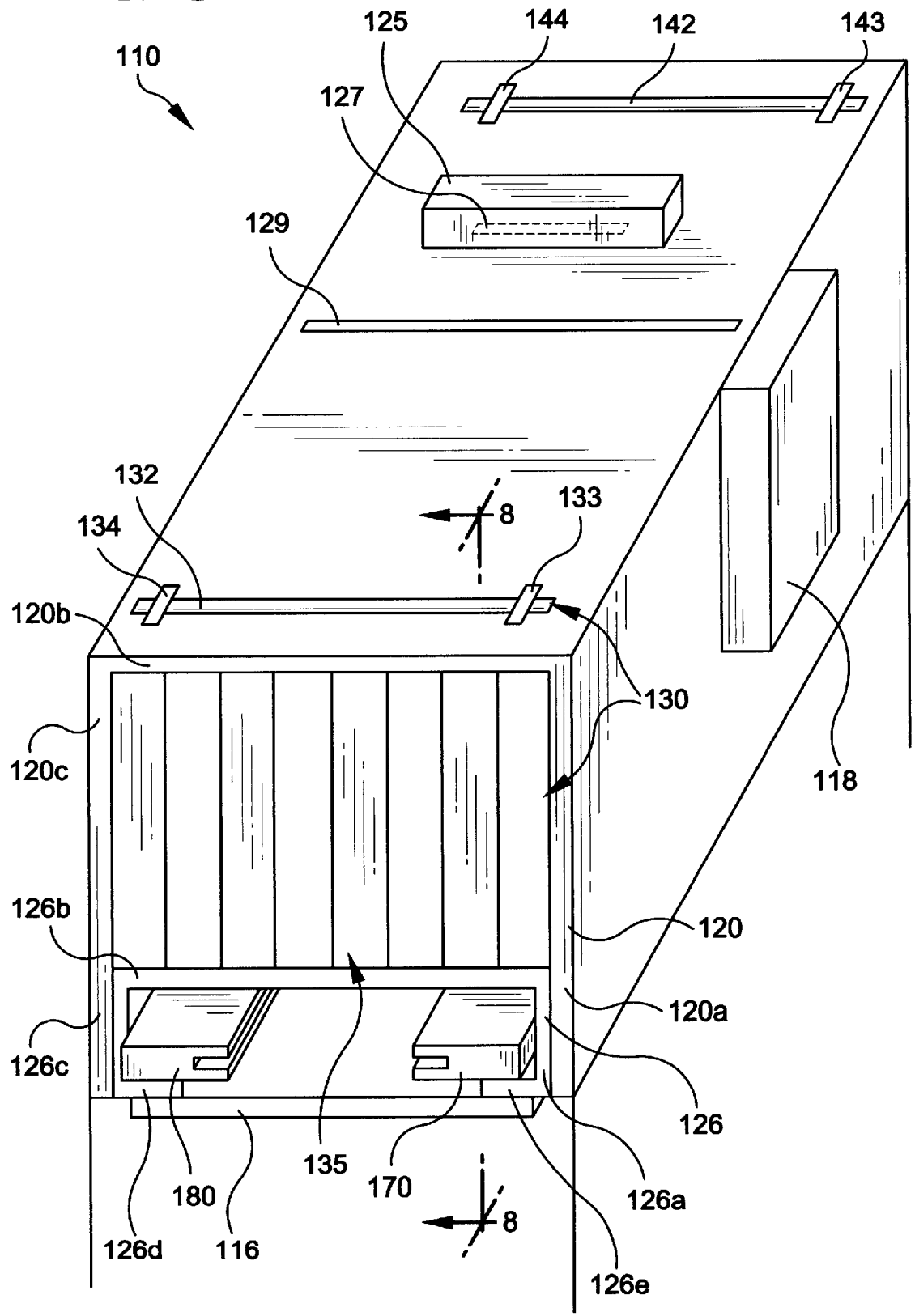
FIG. 3 is a perspective view of the outside of one embodiment of the scanner apparatus and method of the present invention for convenience shown without its rollers or its conveyor belt.
Figure 4:
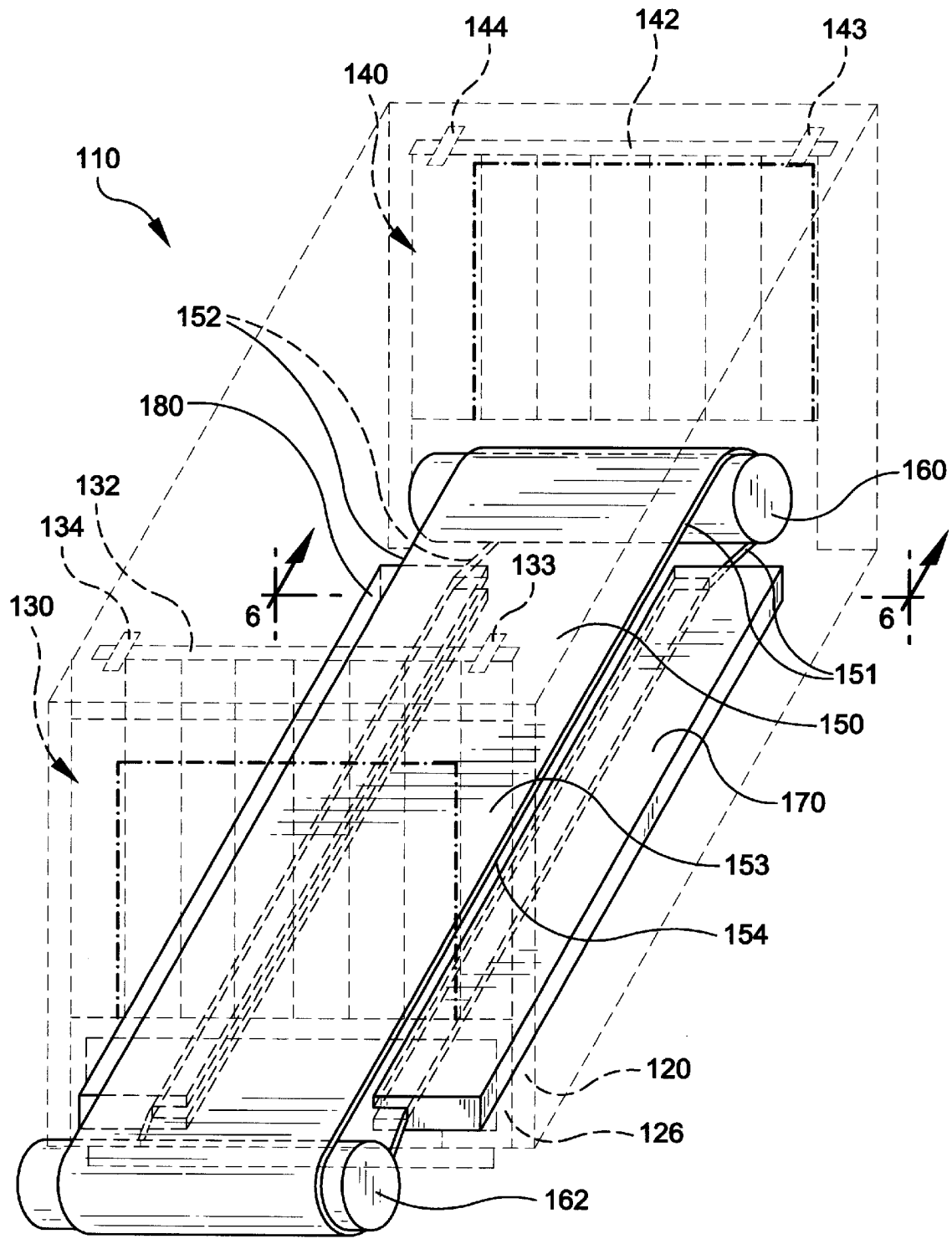
FIG. 4 is a perspective view of the innards of the embodiment of FIG. 3, shown with its rollers and its conveyor belt.

More specifically, FIG. 2 shows a frontal view of a scanner apparatus 110 in accordance with an embodiment of the present invention. FIG. 2 shows the scanner apparatus 110 without a conveyor belt 150 or rollers 160 and 162 as is shown in FIG. 4, to more easily show aspects of this embodiment. The view in FIG. 2 shows a bottom plate 116, detector assemblies 118 mounted on the inside and an empty annulus, inverted U housing 120, bed assembly housing 126, isolating device portion 130, and belt guide rails 170 and 180. FIG. 3 hows an outside perspective view of the scanner apparatus 110, again without the rollers 160 and 162 and without the conveyor belt 150, for convenience of illustration. FIG. 11 shows the same arrangement as FIG.3, but with the detector trays mounted outside.

Although the X-ray collimator means is not shown, it will be understood by those skilled in the art that the invention is applicable to various collimator means including the common continuous fin, the flying spot, scatter collimators, pinhole collimators, CT scan collimators or variations thereof. Where the generator is located anywhere but directly underneath the bed section; a partial slit on one side of the inverted U section is required, for example on the side facing a side-mounted generator, but some slitting will be eliminated in any event if the preferred embodiment is used.

The view of FIG. 3 additionally illustrates an optional vapour detector 125, slot 127, and X-ray slot 129. The detector assembly 118, vapour detector 125, slot 127, and X-ray slot 129 comprise parts of one or more analysis devices. The slot 127 allows vapours to be sensed by the vapour detector 125. The X-ray slot 129 would in practice be covered by either a generator and collimator housing or detector housing which is not shown, such as an electromagnetic detector or generator. If generator, it would be covered by a steel bonnet (not shown), and a detector housing (not shown) would be located below the bed assembly housing 126.

Parts of isolating device portions 130 and 140 are also shown in FIG. 3. FIG. 4 shows an inside perspective view of the scanner apparatus 10 with the rollers 162 and 160 and conveyor belt 150, but without some of the outside components shown in FIG. 3.

The scanner apparatus 110 shown in FIG. 2 has an overall height of $H_{F2}$ and an overall width of $W_{F2}$ which may be the same as $H_{F1}$ and $W_{F1}$ shown in the prior art device of FIG. 1. However, the height $H_{F2}$ and the width $W_{F2}$ for the enclosed area bounded by the tunnel housing 120 and a top portion 126b of the bed assembly housing 126 is considerably greater than the area bounded by the tunnel housing 20 and the top of the bed assembly housing 26 of FIG. 1 of the prior art, i.e. $H_{F2}$ is greater than $H_{F1}$ and $W_{F2}$ is greater than $W_{F1}$. Many aspects of embodiments of the present invention combine to make this increased enclosed tunnel area possible without increasing the overall size of the scanner apparatus 110 from the prior art scanner 10 of FIG. 1.

Among these aspects are the manner of forming and connecting isolating device portions 130 and 140, the compact tracking device comprised of the guide rails 170 and 180, the use of a detector assembly 118 comprised of steel and lead, and connected on one side of the tunnel housing 120, and the reduction of unnecessary framing to provide an essentially frameless construction. These aspects of embodiments of the present invention and other aspects, provide other benefits which will be described further herein.

The reduction of unnecessary framing is an important aspect of the present invention. Instead of using framing as in FIG. 1, the inverted U housing 120 is thickened and the preferred embodiment need not be weakened by detector slits which are placed instead in the interior mounted detector trays. The thickness of the housing 120 will vary depending on the scanner size, and such additional factors as the potential elimination of the sheet lead, which contains x-ray scatter, if the x-ray power is low enough and the steel is thick enough, and the like. In general, the thickness of the housing will range from about 0.0625 to about 0.50 inch. Based on the x-ray power if the desire is to also eliminate the lead sheeting, the thickness of the housing ranges from 0.119 to 0.5 inch. Otherwise, the thickness of the housing ranges from about 0.1 inch to about 0.25 inch. More preferable, where lead shielding will be used to control scatter, are tunnel housing thicknesses ranging from about 0.074 to about 0.12 inch. Most preferable are tunnel housings having thickness of about 0.119 inch. These housings provide, in combination, the advantageous features of reduced complexity, decreased construction and operating costs, and increased operating reliability, and are, accordingly, the most preferred.

The preferably one piece inverted U housing is comprised of side portions 120a and 120c, and a top portion 120b. The side portions 120a and 120c of the inverted U housing 120 are preferably extended down to the bottom of the bed assembly housing 126. The bed assembly housing 126 is comprised of side portions 126a and 126c, top portion 126b, and bottom portions 126d and 126e. The side portions 120a and 120c are then structurally joined, by bolts or otherwise, to side portions 126a and 126c respectively of the bed assembly housing 126. The top portion 126b of the bed assembly 126 preferably provides the bottom or base to the substantially enclosed area bounded by the inverted U housing and the bottom portion 126b.

In this embodiment the bed assembly housing 126 functions as a beam over the enclosed tunnel length and closes the scanner apparatus 110 into a stronger box construction. Lead shielding and wiring is preferably provided on the inside of the inverted U housing 120, unlike the outside as in the prior art. The outside of the inverted U housing 120 can then be painted so that cosmetic panels or frames are not needed. Bolting the inverted U housing 120 to the bed assembly housing 126 also clamps any lead shielding on the inside of side portions 120a and 120c of the inverted U housing 120 firmly at the bottom. Retainers, not shown, may be used to hold the lead under the top portion 120b of the inverted U housing 120. Lead on the inside sides of the inverted U housing 120 can additionally be held by glue, additional retainers or hardware. Low friction tape or the retainers protect any items from the lead shielding, which can also be painted.

The detector assembly 118 is preferably one leaded piece of thinner bent steel construction which carries one full detector array, the other generally being at right angles within the inverted U, and it is preferred that the detector assembly 118 contain the x-ray slit opening, not shown, through which x-rays pass to the detectors. In the alternate embodiment of FIG. 11, a generator shoot diagonally down arrangement, the detector assembly 118 is also preferably located inside the inverted U, or if not, then cosmetically finished outside to dispense with the bulkiness, cost and maintenance for framed outside cosmetic panels which were required by the prior art. The detector assembly 118 is only on one side, and its width is preferably much narrower than the width $W_{S2}$ of the prior art side framing shown in FIG. 1.

Typically the detector assembly 118 can be about one-third, ⅓, the width of the prior side framing $W_{S2}$ Since the prior art required two side framing members, this is a substantial space savings, which may equal for example, at several additional inches available for the width $W_{T2}$ of the inverted U housing 120. The width, $W_{T2}$ is the key dimension allowing larger items to be screened, the length of an item which can travel along a conveyor belt such as a belt 150, is practically unlimited for a conveyorized scanner. The top of the tunnel also needs no framing, in part due to the isolating device portion 130 discussed herein which takes up a very low height, which may be a fifth of the width $W_{B1}$ of the top framing of the prior art. In this manner tunnel height $H_{T2}$ can be increased to 2 or 3 inches more, or the overall height of the machine reduced. In the security field, whenever a scanner can provide the same tunnel throughput size at a narrower width or lesser height, the guards' or operators' vigilance is enhanced because it is less blocked by the scanner. Existing facilities may be able to accommodate one more scanner station for a given width.

Figure 8:
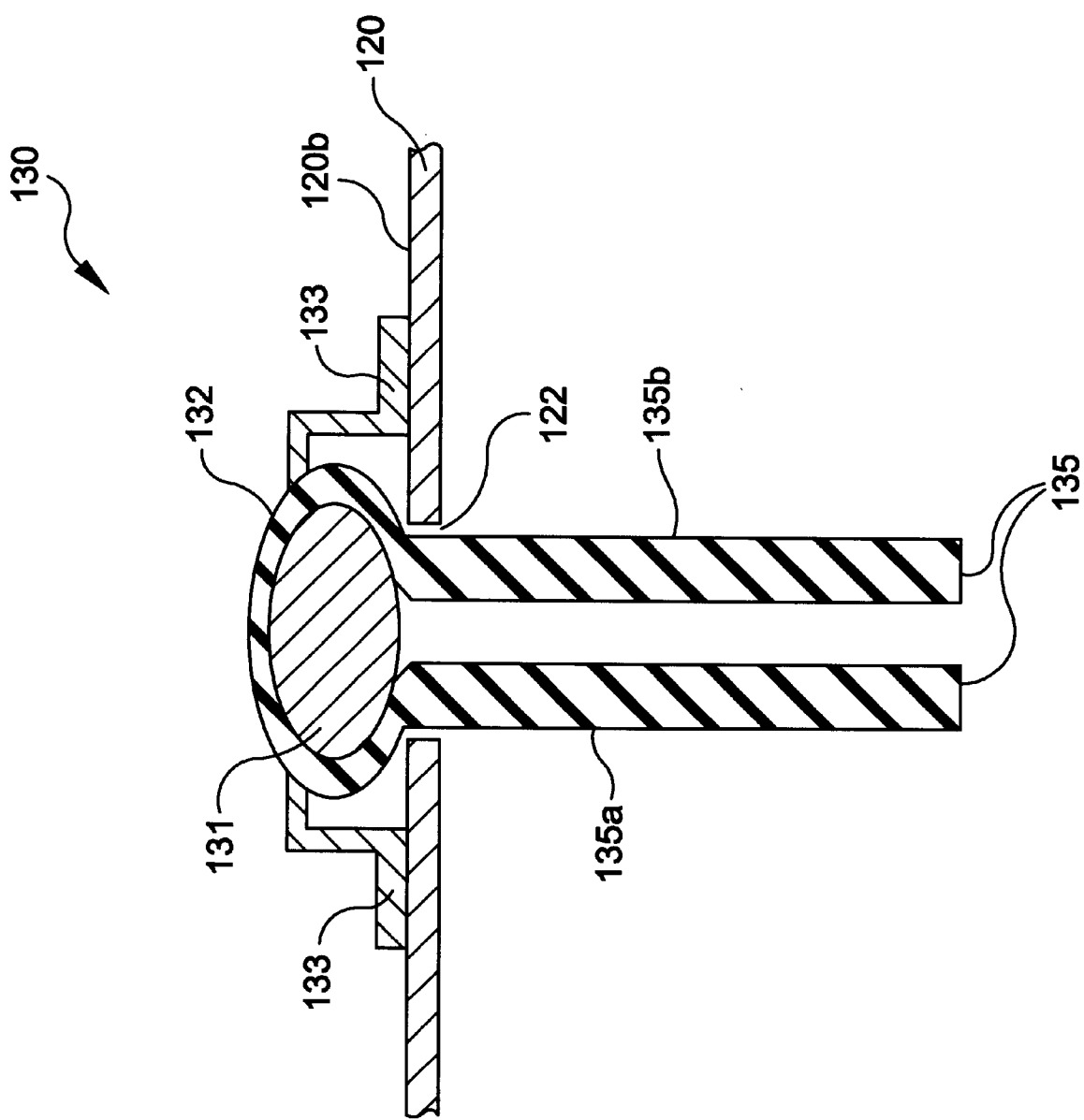
FIG. 8 is a side cross sectional view of a curtain used as part of an isolating device for use with the conveyor device of the embodiment of FIG. 4.
Figure 9:
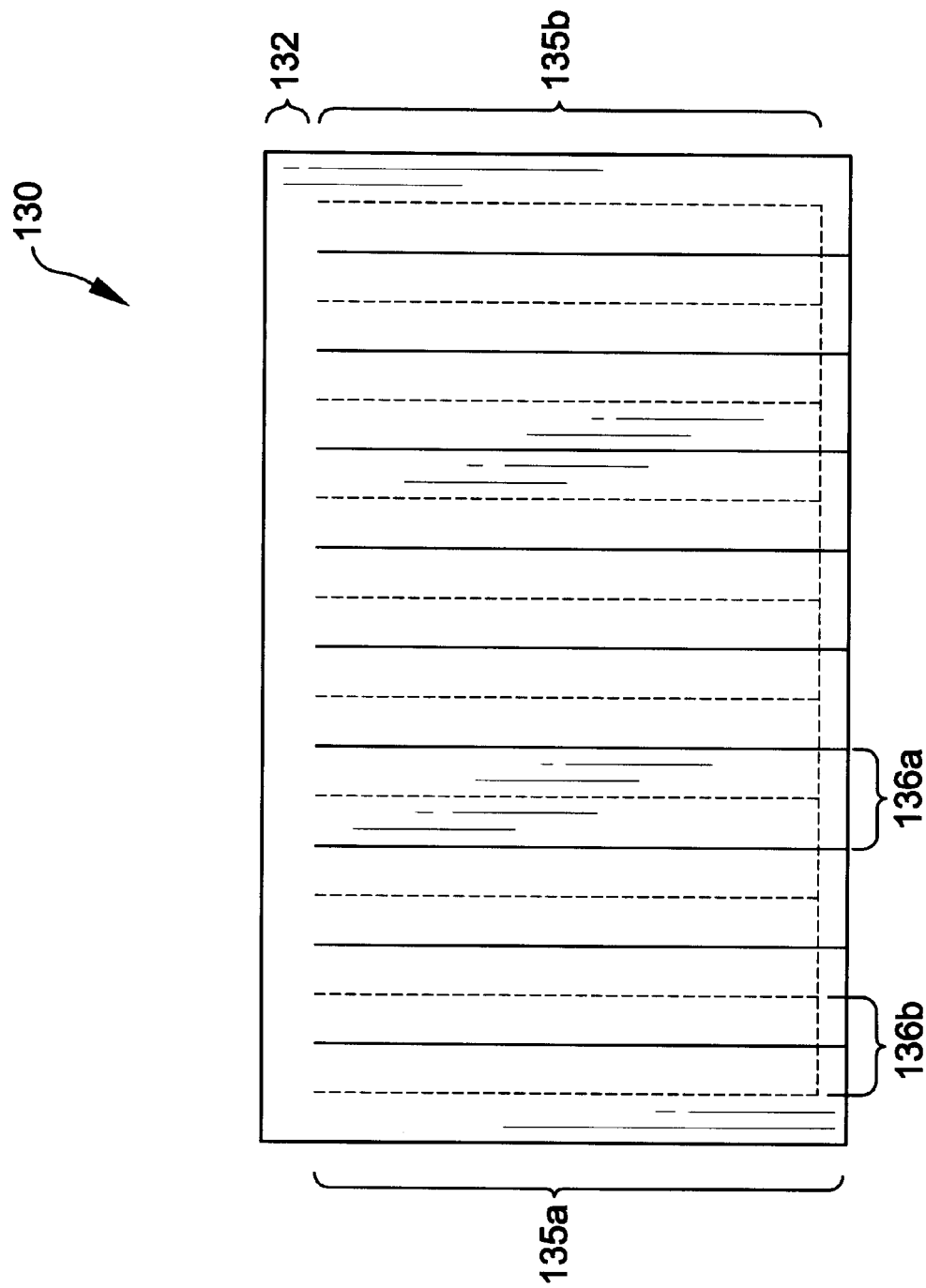
FIG. 9 is a front view of an overlapping configuration for an curtain used as part of an isolating device.

FIGS. 2, 3, 4, 8, and 9 will be used to describe the isolating device portions 130 and 140. FIGS. 8 and 9 show cross sectional and frontal views of the isolating device portion 130. FIG. 8 is a cross sectional view of FIG. 3 taken along line AA. FIG. 9 is a view of the isolating device portion 130 prior to insertion into a slot 122 of the top portion 120b of the tunnel housing 120. Isolating device portions 130 and 140 are preferably substantially the same and therefore only isolating device portion 130 is illustrated in detail in FIGS. 8 and 9.

As shown in FIGS. 3 and 4, isolating device portions 130 and 140 are located at the entrance openings and exit openings, respectively, of the scanner apparatus 110. The isolating device portions 130 and 140 include brackets 131 and 141 and flat curtain portions 135 and 145, respectively, as shown for isolating device portion 130 in the cross sectional view of FIG. 8. The bracket 131 and the rounded curtain portion 132 of the isolating device portion 130 is mounted to the top portion 120b of the tunnel housing 120 of the scanner apparatus 110 by mounting pieces 133 and 134 as shown in FIGS. 3 and 8. The mounting pieces 133 and 134 may be clamp like instruments. Similarly the bracket 141 and the rounded curtain portion 142 of the isolating device portion 140 is mounted to the top portion 120b of the tunnel housing 120 of the scanner apparatus 110 by mounting pieces 143 and 144 as shown in FIG. 3 and is substantially similar to FIG. 8.

The flat curtain portion 135, the curtain portion 132, and the bracket 131 are preferably constructed together and then inserted through a slot 122 in the top portion 120b of the tunnel housing 120 as shown by FIGS. 3 and 8. The bracket 131 and the curtain portion 132 are then preferably mounted to the tunnel housing 120 by mounting pieces 133 and 134 so that there is a tight seal and the slot 122 is completely covered by the bracket 131, curtain portion 132, and the flat curtain portion 135.

The flat curtain portion 135 is preferably comprised of a front section 135a and a rear section 135b. The front section 135a is preferably cut into flaps of material 136a, as shown in FIG. 9. The rear section 135b is preferably cut into flaps of material 136b, as shown by the dashed lines in FIG. 9. The flaps of material 136a and 136b preferably overlap as shown in FIG. 9. The curtain is typically made of lead filled vinyl/fabric laminate. The brackets 131 and 141 can be steel, aluminum, wood, or any material that holds the curtain in place.

The tunnel housing 120 and the isolating device portions 130 and 140 generally provide a completely enclosed area inside the scanner apparatus 110. However, it is not necessary, and in fact may be desirable that portions of the conveyor belt 150 lie outside the enclosed area. In addition, the bed assembly housing 126, although not shown outside the enclosed area, may as known in the art be provided outside the enclosed area. In fact, the FIG. 4 illustration shows the roller 162 and a portion of the conveyor belt 150 outside the enclosed area. The roller 160 may also be outside the enclosed area.

The enclosed area makes the scanner apparatus 110 particularly useful as a security or screening device, where electromagnetic radiation or X-rays are used and it is desirable to have such radiation or X-rays contained. An appended section of plastic housing can be added in front of the isolating device portion 130 and the conveyor belt can be extended further and into the extra plastic housing. This extra plastic housing can be used to prevent an individual from putting his hands into the enclosed area beyond the isolating device portion 130 and inside the tunnel housing 120. The use of a slot 122 for the isolating device portion 130 in the top portion 120b of the tunnel housing 120 allows for the easy attachment of such an extra plastic housing, prior in position, to the isolating device 130. I.e. the extra plastic housing can be attached in front of the isolating device portion 130.

Figure 5:
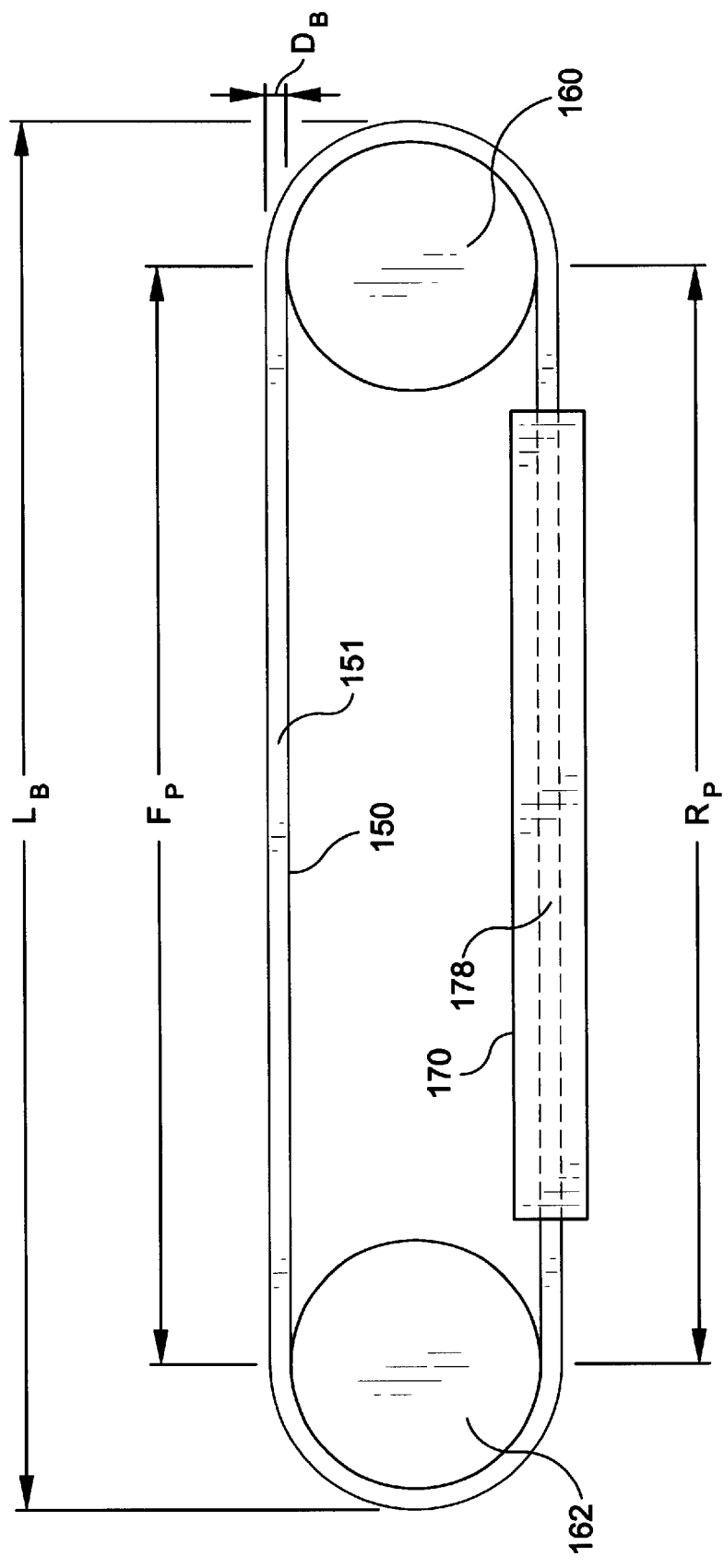
FIG. 5 is a side view of the preferred embodiment for a conveyor belt and tracking device in accordance with the present invention.
Figure 6:
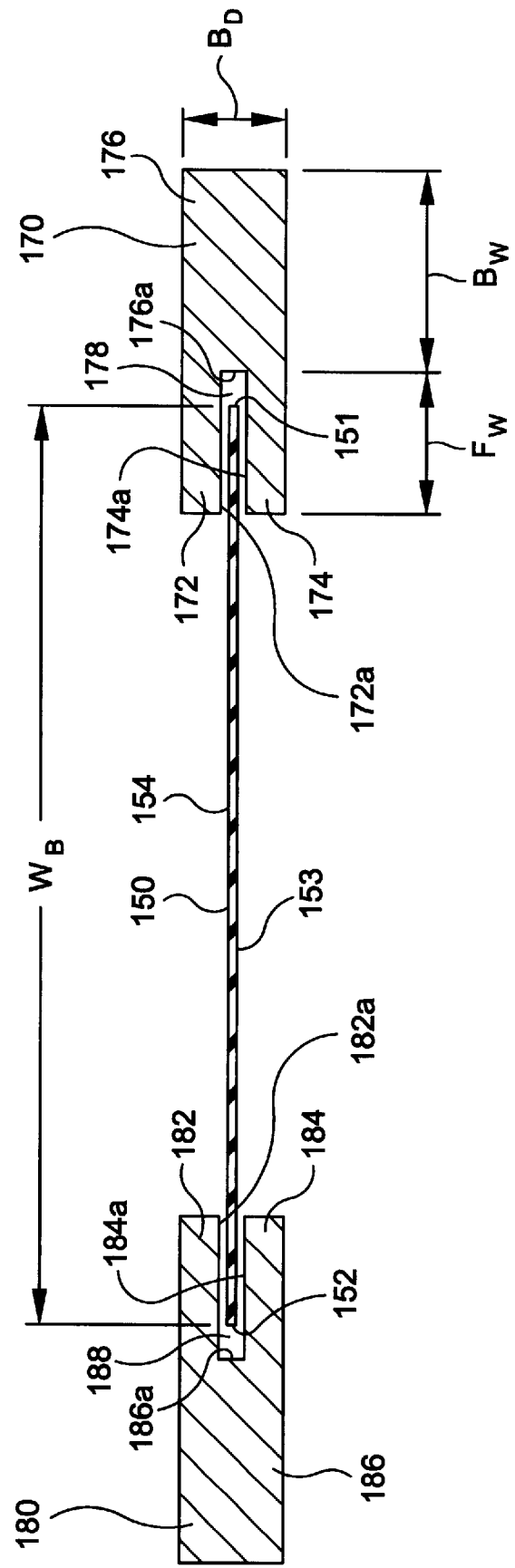
FIG. 6 is a cross sectional view of the tracking device and the portion of the conveyor belt in the return path of the embodiment of FIG. 4.
Figure 7:
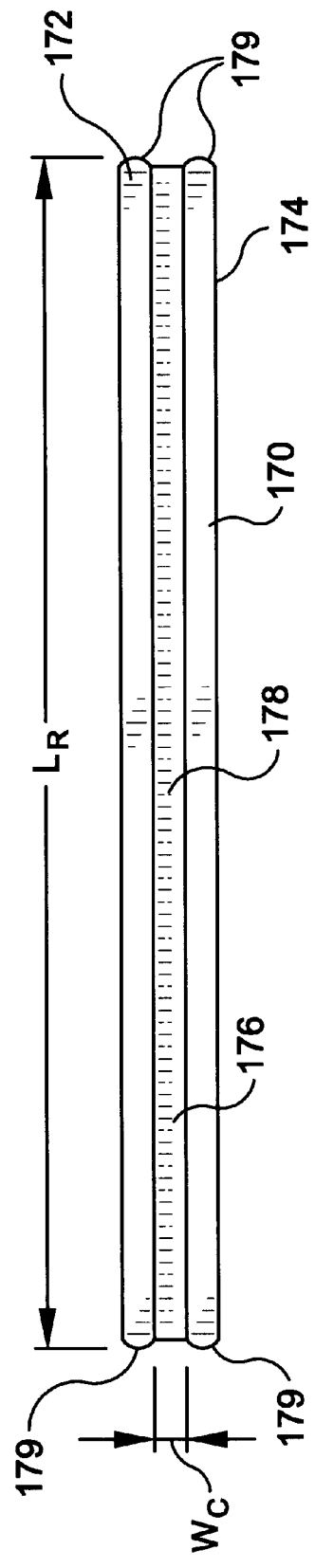
FIG. 7 is a side view of one of the rails for use in the tracking device in the embodiment of FIG. 4.

The inside of scanner apparatus 110 will be described with reference to FIGS. 2, 4, 5, 6, and 7. FIG. 4 is a perspective view of the scanner apparatus 110 with the tunnel housing 120, bed assembly housing 126 and isolating device portions 130 and 140 shown in dashed lines. FIG. 5 is a side view of the conveyor belt 150 and a moving device comprising rollers 160 and 162. FIG. 6 is a cross sectional view of guide rails 170 and 180 and conveyor belt 150, taken along line BB in FIG. 4. FIG. 7 is a frontal view, looking into a channel 178 of the guide rail 170.

The conveyor belt 150, as shown in FIGS. 4, 5, and 6 is typically a belt formed substantially in the shape of a loop. The conveyor belt 150 may be a woven carcass type belt with elastomer covering. The conveyor belt 150 is comprised of a first edge 151, a second edge 152, an outer surface 153, and an inner surface 154, shown in FIGS. 4 and 6. The first edge 151 and the second edge 152 are shown as darkened dashed lines for the portion of the conveyor belt 150 which is in the return path in FIG. 4. The first and second edges 151 and 152 pass through channels 178 and 188 of guide rails 170 and 180, respectively, during the movement or rotation of the conveyor belt 150, as shown in FIGS. 4 and 6. The conveyor belt 150 traverses a forward path, "$F_P$", and a return path, "$R_P$", as shown in FIG. 5. The forward path and the return path may be relatively short, such as for example forty-three inches long each. The conveyor belt has a length "$L_B$" shown in FIG. 5, and a width, "$W_B$", shown in FIG. 6, when it is fully extended over the rollers 160 and 162. The length/width ratio of the conveyor belt 150, or $L_B/W_B$, is preferably less than twelve to one. The length to width ratio can for example be as low as two or three to one or lower. The length $L_B$ may be 47 (forty-seven) inches while the width $W_B$ may be 15.75 inches.

The guide rails 170 and 180, are comprised of inner flanges 172 and 182, outer flanges 174 and 184, and border pieces 176 and 186, respectively. The guide rails 170 and 180 preferably lie entirely between the rollers 160 and 162 as shown in FIG. 4. The inner flange, outer flange, and border piece of each guide rail are preferably constructed as one unit from the same material, but may be constructed in other manners. The material may be a wide variety of materials such as wood, fiberglass, aluminum, steel, nylon, Polypropylene (P.P.), Polyethylene (P.E.), or High Density Polyethylene (H.D.P.E.). The border pieces 176 and 186 are preferably rectangular units having a length, width, and a depth, where the length is greater than the width, and the width is greater than the depth. For example, border piece 176 of guide rail 170 preferably has a length of $L_r$, a width of $B_r$, and a depth of BD as shown in FIGS. 6 and 7. Dimensions of 30.25 inches for the length, two inches for the width, and 0.125 inches for the depth can be used. These dimensions allow the guide rail 70 to be mounted firmly to part of bed assembly housing 121 as shown in FIG. 2, but also to be compact so that the guide rail 170 does not affect other operations or take up too much of the available space for the enclosed tunnel area of the scanner apparatus 110. These dimensions may vary for the length.

The guide rails 170 and 180 are typically rounded off at their edges to allow for a smooth transition and to prevent damage to the belt. For example, guide rail 170 as shown in FIG. 7, has four rounded edges 179, at its two ends.

The width of the channel 178 is shown in FIG. 7 as $W_C$, and is preferably slightly greater than the depth of the conveyor belt, $D^B$, which is shown in FIG. 5. For a typical X-ray scanner, the width of the channel may be about 0.19 inches while the depth of the conveyor belt may be about 0.125 inches, and proportionally larger for a thicker conveyor belt. The width of the channel 188 preferably has similar dimensions. These dimensions for the channels 178 and 188 provide an appropriate amount of clearance and control of the conveyor belt 150. The inner flanges and outer flanges preferably overlap the conveyor belt 150 by a length of $F_W$, which may be 0.625 inches, minus the clearance between the edge 151 of the conveyor belt and the surface 176a of the border piece 176, which clearance may be ⅛ (one-eighth) of an inch. This overlap length provides an appropriate amount of control to prevent the conveyor belt 150 from buckling.

The rollers 160 and 162 are preferably rotatably mounted to the tunnel housing 120 and/or bed assembly housing 126 by bearings in a manner known to those skilled in the art.

In operation, a person inserts an object, such as a purse, through the flat curtain portion 135 of the isolating device portion 130. The flat curtain portion 135 is preferably made of a flexible material and is typically not mounted to the top portion of the bed assembly housing 126b, so that an object can be inserted. The object is placed on the conveyor belt 150 and passes through the isolating device portion 130. The conveyor belt 150 can be caused to rotate or move by any manner known in the art. The object is transported by the conveyor belt 150 to the exit of the scanner apparatus 110, and past the isolating device portion 140.

During the movement of the conveyor belt 150 the inner flange 172 has a surface 172a which is substantially parallel and substantially adjacent to a portion of the inner surface 154 of the conveyor belt 150 as shown in FIG. 6. The outer flange 174 has a surface 174a which is substantially parallel and substantially adjacent to a portion of the outer surface 153 of the conveyor belt 150 as also shown in FIG. 6. The border piece 176 has a surface 176a which during the movement of the conveyor belt 150 is substantially parallel to a part of the first edge 151 of the conveyor belt 150. In normal operation, the first edge 151 is preferably about ⅛ (one-eighth) of an inch from the surface 176a. The second edge 152 is preferably a similar distance form the surface 186a in normal operation. This allows for a certain amount of clearance. The inner flange 182, outer flange 184, and border piece 186 have similar surfaces 182a, 184a, and 186a. A portion of the inner surface 154 of the conveyor belt 150 which at one time is in the channel 178, eventually comes in contact with the rollers 160 and 162. Similarly a portion of the inner surface 154 of the conveyor belt 150 which at one time is in the channel 88, eventually comes in contact with the rollers 160 and 162.

During the movement of the conveyor belt 150, due to the low length to width ratio, the first and second edges, 151 and 152 respectively, of the conveyor belt 150 may drift. For example, the first edge 151 may drift far enough to come in contact with the surface 176a of the border piece 176. When this drifting occurs, the conveyor belt is prevented from becoming further misaligned by the inner flange 172, outer flange 174, and the border piece 176. The border piece 176 prevents the conveyor belt 150 from drifting further. The inner flange 172 and outer flange 174 prevent the conveyor belt 150 from bending substantially after the first edge 151 contacts the surface 176a of the border piece 176. The inner flange 182, outer flange 184, and border piece 186 preferably provide the same function when the second edge 152 of the conveyor belt 150 drifts towards the border piece 186.

Figure 10:
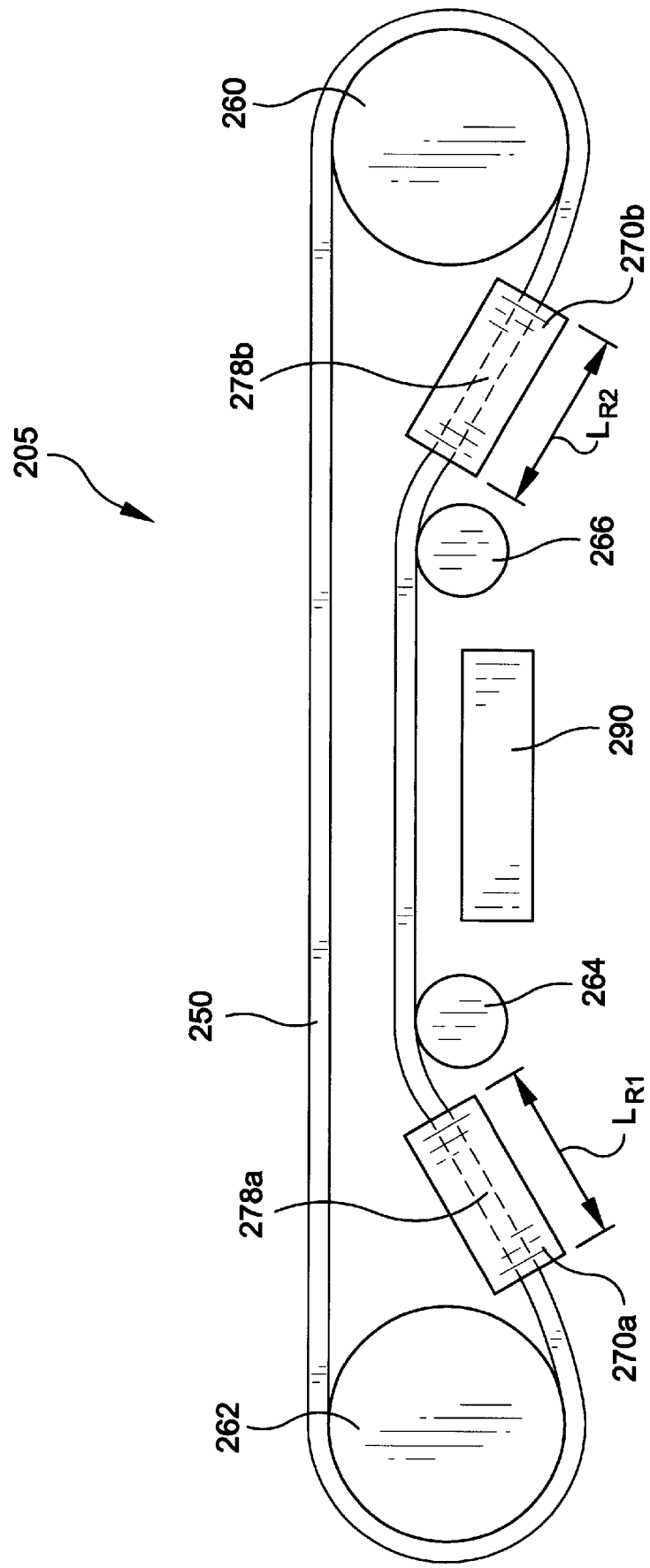
FIG. 10 is a side view of a conveyor belt and tracking device for use with the embodiment of FIG. 4.

FIG. 10 is a side view of another embodiment for a tracking device 205 preferably for use with a scanner apparatus similar to scanner apparatus 110 in accordance with the present invention. Tracking device 205 includes conveyor belt 250, preferably motorized rollers 260 and 262, idle rollers 264 and 266, and guide rails 270a and 270b. Also shown is an obstacle 290, around which the conveyor belt 250 winds. In the tracking device 205 the guide rails 270a and 270b are preferably about five inches in length $L_{R1}$ and $L_{R2}$. There are also preferably guide rails 280a and 280b, which are not shown, but which are located on the other side of conveyor belt 250, which are preferably mirror images of guide rails 270a and 270b. The guide rails 280a and 280b serve a similar function to the guide rail 180 in FIG. 3. The guide rails 270a, 270b, 280a, and 280b are preferably mounted on inclined brackets.

The present invention in its various embodiments solves many problems of the prior art dealing with scanner apparatus and methods. However, those skilled in the art will recognize that various aspects of the present invention can be put to uses other than in scanning apparatus and methods.

The improved tracking aspect provides an economical means of automatic, mechanical conveyor belt tracking, preferably using a standard specification belt. The simpler automatic tracking mechanism also makes it easier to design tilt up conveyor bed ends, which protrude out from the tunnel, for more compact transport of the scanning apparatus by freight carriers or in elevators. The improved isolating aspect of embodiments of the present invention provides an improved means of fitting an isolation curtain to a housing, in a manner which simplifies the construction of the device, facilitates its assembly and disassembly for replacement or field servicing, and reduces framing cost and size.

In scanner configurations where one of the analysis devices includes a generator, there typically, as known in the art, will be at least one X-ray slit which in some embodiments, such as FIG. 11, can be buttressed by a collimator housing assembly which also collimates the X-rays from the generator or by a detector housing assembly. Such an X-ray slit may be in the location of FIG. 3, X-ray slot 129. Embodiments of the invention can be used for hand carried parcel scanners screening items in size up to hand luggage, garment bags, backpacks, large brief cases, amorphous prison mattresses, etc., as much as the larger sizes which may require thicker tunnel housing.

The analysis devices provided may include an explosive's vapour detector in the position of the detector 125 in the embodiment of FIG. 3. This vapour detector makes use of the relatively tight seal of air around the parcel scanned within the constricted size tunnel and lead x-ray curtains on either end. Any side of the tunnel housing can be slitted and fitted with one of many types or makes of explosives, vapour detectors which suck in by air pump a sample of air and particulates, to analyze them for the presence of explosives, drugs or contraband, while the parcel is in the tunnel being x-rayed. The vapour detector casing would have to be lead shielded for X-ray scatter. The preferred location to mount the vapor detector to maintain compactness would be above the enclosed area bounded by the tunnel housing and the top portion 126b of the bed assembly housing 126, preferably away from the line which bisects the tunnel housing, along which usually runs an X-ray fan or flying spot slit upon which is mounted either the generator or a detector array. This is the location of detector 125 shown in FIG. 3. The area and dimensions of the vapour access slit would be determined by the internal air pump and hose attachment of the detector selected. Less compact arrangements could also be made out the tunnel sides. Venting through the bottom of the tunnel is also possible, but would be complicated by the placement of the moving conveyor belt.

Having thus described the invention in rather full detail, it will be that such detail need not be strictly adhered to but that various changes and modifications may suggest themselves to one skilled in the art, all falling within the scope of the present invention, as defined by the subjoined claims.

We claim:

1. A scanner apparatus comprising:
   a tunnel housing comprised of:
      a top portion, and first and second side portions, an entrance opening and an exit opening;
      a bed assembly housing comprised of a top portion which together with the tunnel housing forms a substantially frameless, substantially enclosed area,
      an isolating device located at the entrance and exit openings of the tunnel housing;
      a conveyor device for moving an object through the entrance opening of the tunnel housing and into the substantially enclosed area, subsequently through the substantially enclosed area, and thereafter out of the substantially enclosed area and out the exit opening of the tunnel housing, the conveyor device located substantially in the bed assembly housing; and
      an analysis device for analyzing objects within the substantially enclosed area of the tunnel housing; and
      means for increasing portabillity comprising the top portion and side portions of the tunnel housing each have a thickness ranging from about 0.065 to about 0.5 inch.

2. A scanner apparatus, as recited by claim 1, wherein said bed assembly further comprises first and second side portions and wherein said first and second side portions of said tunnel housing are substantially fixed to said first and second side portions of said bed assembly housing, respectively.

3. A scanner apparatus, as recited by claim 1, wherein said analysis device is comprised of an internally mounted detector array constructed within a metal member which contains a detector slit, to reduce the slitting of said tunnel housing.

4. A scanner apparatus, as recited by claim 1, wherein said tunnel housing further comprises:

a. a first slot in one of its portions near its entrance opening, and
   b. a second slot in one of its portions near its exit opening; and wherein said isolating device comprises:
   c. a first bracket having a first curtain extending from it, said first bracket and said first curtain and said first slot of said tunnel housing being adaptable so that said first curtain can be inserted into and through said first slot but said first bracket cannot be inserted through said first slot, said first curtain, alter insertion, being adapted to substantially cover the entrance opening of said tunnel housing, said first bracket, after insertion, being substantially fixed to a portion of said tunnel housing,; and
   d. a second bracket having a second curtain extending from it, said second bracket and said second curtain and said second slot of said tunnel housing being adaptable so that said second curtain can be inserted into and through said second slot but said second bracket cannot be inserted through said second slot, said second curtain, after insertion, being adapted to substantially cover said exit opening of said tunnel housing, said second bracket, after insertion, being substantially fixed to a portion of said tunnel housing.

5. A method for constructing a scanner for scanning objects, comprising the steps of:
   a. constructing a tunnel housing comprised of a top portion, a bottom portion, first and second side portions, which form a substantially enclosed area, an entrance opening and an exit opening, said top portion and side portions of said tunnel housing each having a thickness ranging from about 0.0625 to 0.5 inch;
   b. constructing a bed assembly housing located substantially beneath said bottom portion of said tunnel housing, said bed assembly housing being constructed so that said bed assembly has a top portion which is substantially used as said bottom portion of said tunnel housing;
   c. locating an isolating device at said entrance and exit openings of said tunnel housing;
   d. locating a conveyor device substantially in said bed assembly housing, said conveyor device being used for moving an object through said entrance opening of said tunnel housing and into said substantially enclosed area, subsequently through said substantially enclosed area, and thereafter out of said substantially enclosed area and out said exit opening of said tunnel housing; and
   e. providing an analysis device for analyzing objects within said substantially enclosed area of said tunnel housing.

6. A method as recited by claim 5, further comprising the steps of:
   a. constructing said bed assembly housing so that said bed assembly housing has first and second side portions; and
   b. fixing said first and second side portions of said bed assembly housing to said first and second side portions of said tunnel housing, respectively.

7. A method for constructing a scanner for scanning objects, as recited by claim 5, further comprising the step of using said analysis device to connect said tunnel housing with said bed assembly housing.

8. A method for constructing a scanner for scanning objects, as recited by claim 5, further comprising the steps of:
- a. providing a first slot in one of the portions of said tunnel housing near its entrance opening; and
- b. providing a second slot in one of the portions of the tunnel housing near its exit opening;

and wherein said step of locating said isolating device comprises:
- a. inserting a first bracket having a first curtain extending from it, through said first slot
- b. substantially fixing said first bracket to a portion of said tunnel housing near said entrance opening of said tunnel housing;
- c. inserting a second bracket having a second curtain extending from it, through said second slot; and
- d. substantially fixing said second bracket to a portion of said tunnel housing near said exit opening of said tunnel housing.

* * * * *